United States Patent [19]  [11]  4,041,952
Morrison, Jr. et al.  [45]  Aug. 16, 1977

[54] ELECTROSURGICAL FORCEPS

[75] Inventors: Charles F. Morrison, Jr., Boulder; Alan Z. Puszman, Lyons, both of Colo.

[73] Assignee: Valleylab, Inc., Boulder, Colo.

[21] Appl. No.: 664,061

[22] Filed: Mar. 4, 1976

[51] Int. Cl.² .......................... A61B 17/36; A61N 3/06
[52] U.S. Cl. ........................... 128/303.13; 128/303.17; 200/61.58 R; 200/157
[58] Field of Search ....................... 128/303.13, 303.14, 128/303.17, 303.18, 404, 405; 200/61.58 R, 157

[56] References Cited

U.S. PATENT DOCUMENTS

| 1,071,978 | 9/1913 | White | 128/303.13 |
| 2,012,937 | 9/1935 | Bevoy | 128/303.14 |
| 3,054,405 | 9/1962 | Tapper | 128/303.18 |
| 3,058,470 | 10/1962 | Seeliger et al. | 128/303.14 |
| 3,643,663 | 2/1972 | Sutter | 128/303.17 |
| 3,911,241 | 10/1975 | Jarrard | 128/303.17 X |

OTHER PUBLICATIONS

Rosenberg, "A New Bipolar Forceps for Electrocoagulation," Plastic & Reconstructive Surgery, vol. 48, No. 4, 1964, p. 390.

Primary Examiner—Robert W. Michell
Assistant Examiner—Lee S. Cohen
Attorney, Agent, or Firm—Gerald J. Ferguson, Jr.; Joseph J. Baker

[57] ABSTRACT

An electrosurgical forceps including a switching member disposed on only one tine thereof where the switching member may be disposed on the outside of the tine to permit operation thereof independent of the closing of the forceps or where the switching member is disposed on the inside of the tine such that the electrical contacts thereof are provided with an electrically insulative covering. There are also provided unique circuit paths on the tines whereby the forceps may be operated in either a monopolar mode with or without switching or a bipolar mode with or without switching. Also disclosed is a spacer for separating the tines and a removable sleeve which snaps over the spacer to hold the tines in place. Further, there is disclosed a double molding method for constructing an electrosurgical forceps or the like.

13 Claims, 17 Drawing Figures

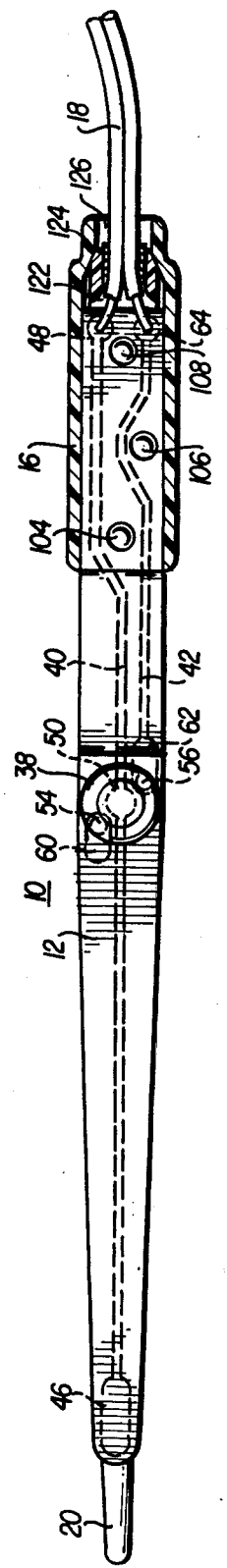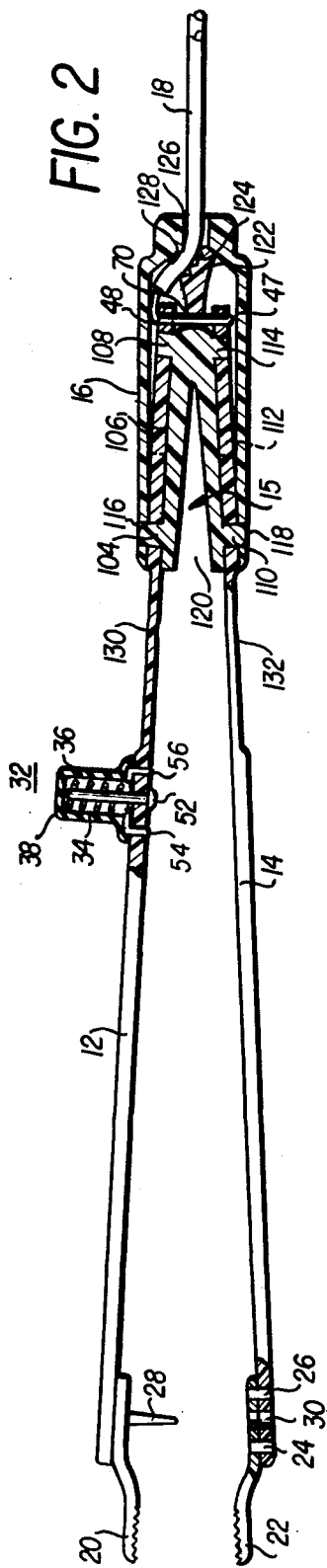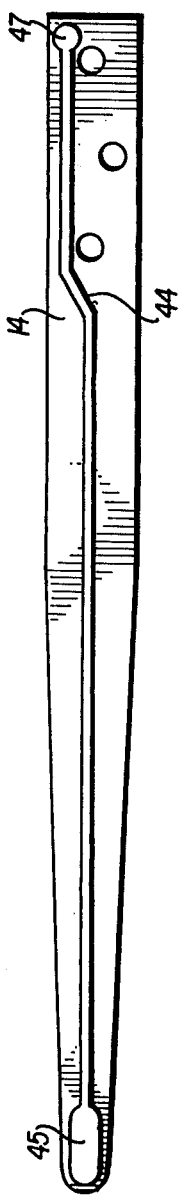

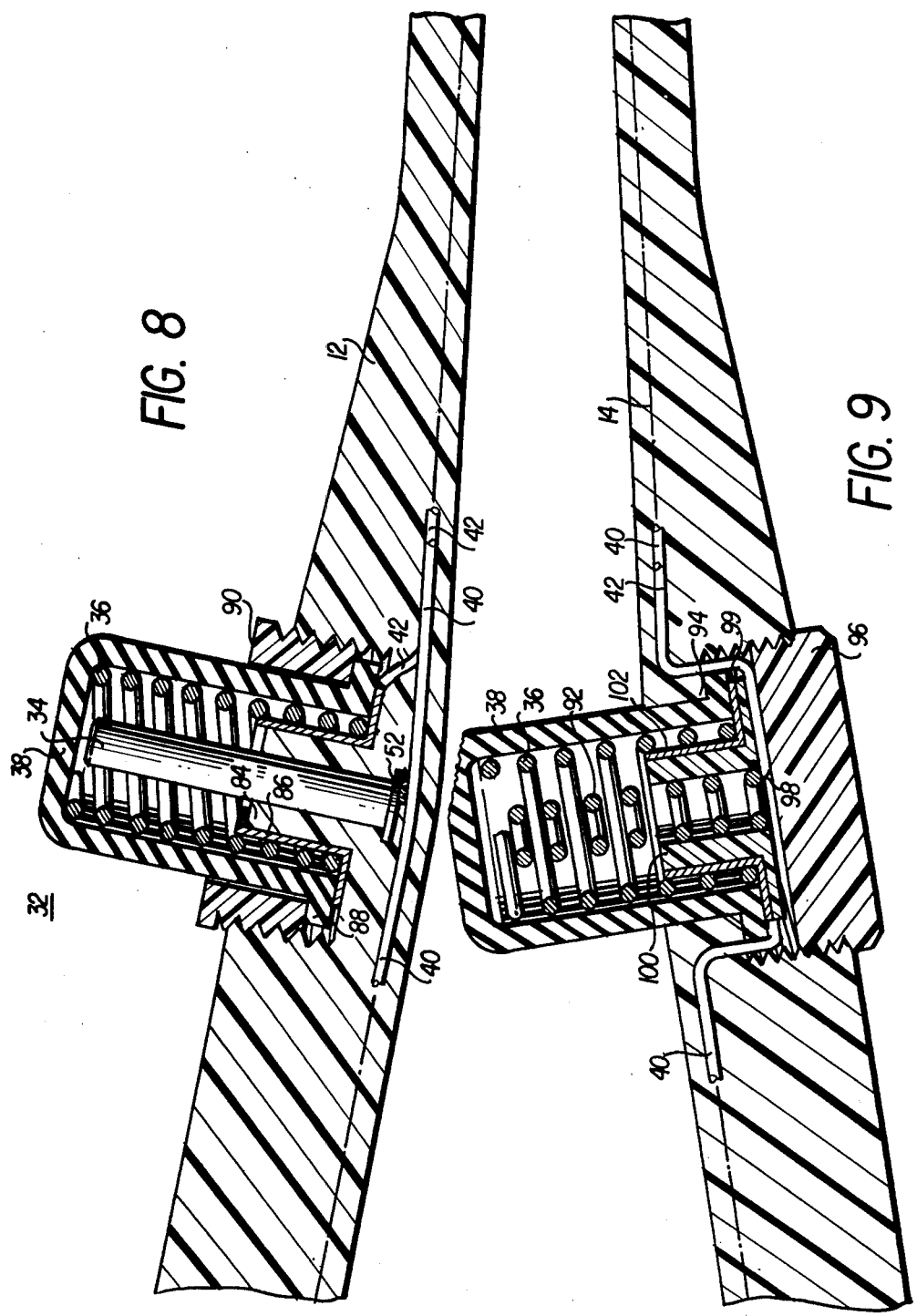

ELECTROSURGICAL FORCEPS

BACKGROUND OF THE INVENTION

1. Field of the Invention

This invention relates to improved electrosurgical forceps and a method of making the same.

2. Discussion of the Prior Art

Heretofore, some electrosurgical forceps have been characterized by the forceps disclosed in U.S. Pat. No. 3,100,489 granted to R. W. Bagley, which patent is incorporated herein by reference. In this type of forceps, switching means are provided on the forceps itself whereby upon closure of the forceps, the swtiching means is closed to thereby permit the application of radio frequency electrical energy to a site to be treated. There are several shortcomings in this type of arrangement. First, the closing of the switch is dependent upon the closing of the forceps. This limits the flexibility available to the physician. Preferably, at least in some instances, the closing of the switch should be independent of the closing of the forceps.

Further, in the prior art devices, the contacts of the switch on the forceps have been exposed to permit engagement thereof when the forceps are closed. However, since the potentials on these exposed contacts can be substantial, there is a certain degree of danger associated therewith.

SUMMARY OF THE INVENTION

It is thus an important object of this invention to provide an improved electrosurgical forceps having a switching means mounted thereon where the switching means can be operated independently of the closing of the forceps.

It is a further object of this invention to provide an improved electrosurgical forceps of the above type where the switching means is mounted on only one tine thereof where the switching means may be either on the inside or the outside of the tine.

It is a further object of this invention to provide an improved electrosurgical forceps of the above type where the contacts of the switching means are provided with an electrically insulative covering so that they are not exposed.

It is a further object of this invention to provide an improved electrosurgical forceps having means for separating and holding the tines in place where the latter means may be readily and economically assembled or taken apart.

Further objects and advantages of the invention will become apparent from a reading of the following specification and claims taken with the drawing.

BRIEF DESCRIPTION OF THE DRAWING

FIG. 1 is a partial cross-sectional, plan view of an illustrative forceps in accordance with the invention.

FIG. 2 is a partial cross-sectional, side view of the forceps of FIG. 1.

FIG. 3 is a plan view of the inside of one of the tines of the forceps of FIG. 1 illustrating a printed circuit path thereon.

FIG. 4 is a schematic diagram of an illustrative wiring arrangement when the forceps of FIG. 1 are employed in a monopolar mode with switching.

FIG. 5 is a schematic diagram of an illustrative wiring arrangement when the forceps of FIG. 1 are employed in a monopolar mode without switching.

FIG. 6 is a schematic diagram of an illustrative wiring arrangement when the forceps of FIG. 1 are employed in a bipolar mode with switching.

FIG. 7 is a schematic diagram of an illustrative wiring arrangement when the forceps of FIG. 1 are employed in a bipolar mode without switching.

FIG. 8 is a partial cross-sectional view of a modified embodiment of the switching assembly of FIG. 1.

FIG. 9 is a partial cross-sectional view of a further switching assembly where the assembly is mounted on the inside of a forceps tine, FIGS. 8 and 9 being so disposed with respect to each other as to illustrate the operation of the switching assembly of FIG. 9 when the forceps are closed.

FIG. 10 is a cross-sectional view of an illustrative modified tine.

FIGS. 11-14 are cross-sectional views of illustrative modified tines made in accordance with a double molding process in accordance with the invention.

FIG. 15 is a plan view of a molded fork assembly preparatory to the second molding step in a double molding process in accordance with the invention.

FIGS. 16 and 17 are cross-sectional views respectively taken along the lines 16—16 and 17—17 of FIG. 15.

DETAILED DESCRIPTION OF THE PREFERRED EMBODIMENT OF THE INVENTION

Reference should be made to the drawing where like reference numerals refer to like parts.

In FIGS. 1 and 2, there is shown an illustrative embodiment of an assembled surgical forceps 10 in accordance with the invention. The forceps generally include a first tine 12 and a second tine 14. The tines are spaced apart by a spacer generally indicated at 15 and are held together by a sleeve 16 in a manner which will be described in more detail hereinafter. The forceps are connected to an electrical cord 18, the wiring of which depends on the mode of operation in which the forceps are used, as will also be described in more detail hereinafter. A pair of electrically conductive tips 20 and 22 are respectively connected to tines 12 and 14, the connection of tip 22 being illustrated in FIG. 2 where a pair of tubular rivets 24 and 26 may be employed. A plastic alignment pin 28 may be provided on tip 20 for engagement with an opening 30 in tip 22 when the forceps are closed. The tips 20 and 22 may be made from stainless steel.

In accordance with an important aspect of the invention, a switch assembly generaly indicated at 32 is disposed on the outside of tine 12. The switch assembly includes a center post electrical contact 34, a spring electrical contact 36 which may be made of beryllium copper or the like and a flexible covering or cap 38 made from an electrically insulative material.

In accordance with another aspect of the invention, the tines 12 and 14 may comprise circuit boards with electrical circuit paths printed on the inner surfaces thereof where it is preferable to cover the circuit paths with an appreciable insulative material. For example, the forceps may be dip-coated to about ½ inch above sleeve 16. Of course, the active areas of tips 20 and 22 would have the insulative material such as plastic removed therefrom to provide patient contact.

Circuit paths on tine 12 are shown in dotted lines at 40 and 42 while a circuit path for tine 14 is shown at 44 in solid lines in FIG. 3. FIG. 3 shows the inside of tine 14, where the circuit path 44 extends from a pad 45 which electrically contacts tip 22 to a terminal 47 which engages one of the wires of cord 18, as will be explained in more detail hereinafter.

Referring to circuit path 40 on tine 12 on FIG. 1, this path extends from pad 46 where it contacts tip 20 to a terminal 48 where it is connected to one of the wires of cord 18. At an intermediate point 50 on the path 40, the path may be somewhat enlarged as a pad and at this point, the center post electrical contact 34 may be soldered to pad 50 as indicated at 52 in FIG. 2. The ends 54 and 56 of spring 36 are respectively soldered to tine 12 at pads 60 and 62 as shown in FIG. 2. Pad 62 is disposed at one end of circuit path 42. The other end of path 42 is disposed at a terminal 64 where connection may be made to another wire of cord 18. Flexible cap 38 may be glued to tine 12.

Reference should now be made to FIGS. 4 through 7 where there are illustrated various wiring diagrams for making connections to the circuit paths 40 through 44 in accordance with the mode of operation of the forceps. In the embodiments of FIGS. 4 and 6, the switching means 32 is employed. As known in this art, such switching means may be employed to enable the operator to energize the forceps only after the switch has been manually actuated. An illustration of circuitry appropriate for effecting this is described in the aforementioned patent to Bagley. Thus, in FIG. 4, which is directed to a monopolar embodiment with switching, wires 66 and 68 would respectively correspond to wires 25 and 26 shown in FIG. 1 of Bagley. Further, wire 66 would be connected by soldering, for example, to terminal 64 of path 42. Wire 68 would be connected to terminal 48, which may comprise an eyelet, and then extend through an opening 70 in spacer 15 to terminal 47, as shown in FIG. 2.

In the non-switching, monopolar embodiment of FIG 5, a single wire 72 from the active side of the electrosurgical generator (not shown), would contact terminals 47 and 48, as described above, for the FIG. 4 embodiment and as shown in FIG. 2. There is no need for switch assembly 32 in the FIG. 5 embodiment. The return side of the generator would be connected to an indifferent electrode positioned adjacent the patient's body in both the FIG. 4 and 5 embodiments, as is well known in this art.

Referring to the bipolar switching embodiment of FIG. 6, the wires 74 and 76 of cord 18 respectively correspond to the wires 25 and 26 shown in FIG. 1 of the aforementioned Bagley patent. Wire 74 would be connected to terminal 64 of path 42 of FIG. 1. Wire 76 would be connected to terminal 48, while wire 78, which is connected to the return side of the generator, would be connected to terminal 47 shown in FIG. 3.

Referring to the bipolar non-switching embodiment shown in FIG. 7, wire 80 from the active side of the generator is connected to terminal 48 while wire 82 from the generator return side is connected to terminal 47.

Thus, it can be seen that the unique arrangement of circuit paths on tines 12 and 14 enable the forceps to be operated in any of four different modes of operation. Also, as can be appreciated from the foregoing description, the number of wires comprising cord 18 will vary depending upon the desired mode of operation where in the FIG. 5 embodiment, cord 18 includes one wire, in the FIG. 4 and 7 embodiments, it includes two wires and in the FIG. 6 embodiment, it includes three wires.

Referring to FIGS. 8 and 9, there are shown further embodiments of switching assembly 32. The embodiment of FIG. 8 corresponds to that of FIG. 1; however, the mounting and electrical connections for the switch assembly are somewhat different. In the FIG. 8 embodiment, wires are embedded in tine 12 rather than printed thereon as in FIG. 1. The method of embedding these wires in the tines is another important aspect of this invention and will be described in more detail hereinafter. A threaded opening is provided on the outside of tine 12, the opening having an annular projection 84 upwardly extending from the bottom thereof. Disposed within and extending from projection 84 is post 34 which is connected by spot welding, for example to wire 40 at 52. An annular electrically conductive spring base 86 is disposed about projection 84. Base 86 is flanged at the bottom thereof to support spring 36. Also disposed on spring base 86 is flexible cap 38 which is flanged at the bottom thereof at 88. The entire switching assembly is secured in place by a retaining bushing 90. Wire 42 is connected by soldering, for example, to spring base 86 to thereby provide an electrical connection between spring 36 and wire 42.

Referring to FIG. 9, a modification of the switching assembly is illustrated. In particular, two important modifications are shown. First, the assembly 32 is mounted on the inside of a tine rather than on the outside thereof as shown in FIGS. 1 and 8. Second, the inner post 34 of the FIG. 8 embodiment is replaced with a spring electrical contact 92. The inside mounting of switching means 32 will be discussed first. It should be noted that FIGS. 8 and 9 have been so drawn that the tine of FIG. 8 corresponds to tine 12 of FIG. 2 while the tine of FIG. 9 corresponds to tine 14 thereof. It should also be noted that the wires 40 and 42 of FIG. 1 may either be in tine 12 or tine 14 while the wire 44 of tine 14 in FIG. 2 would be in the other tine depending on which tine the wires 40 and 42 are disposed in. Thus, in FIG. 9, wires 40 and 42 are shown in tine 14. It should further be appreciated that if the inside mounting of switch 32, as shown in FIG. 9, is employed, the outside mounted switch shown in FIG. 8 need not be employed. Of course, the opposite is true — that is, if the outside mounted switch of FIG. 8 is employed, the inside switch of FIG. 9 need not be used.

Since switch assembly 32 of FIG. 9 is mounted on the inside of tine 14, it will be actuated whenever tines 12 and 14 are brought together, as will be described in more detail hereinafter. An opening extends through tine 14. The opening is stepped as indicated at 94. Flexible caps 38 extends through the opening and is flanged at the bottom thereof to engage the stepped portion 94. A retaining cap 96 is threaded into the opening to support and retain the switch assembly. Wire 42 is electrically connected to inner spring 92 at 98. A flanged, annular insulator 100 is disposed on wire 42 and a flanged, electrically conductive annular spring base 102 is disposed about the insulator 100. The wire 40 is connected to base 102 at 99 whereby a continuous electrical path is provided for wire 40 through base 102 and spring 36. Insulator 100 insulates springs 36 and 92 from one another when switch 32 is in its unactuated state.

Reference should now be made to FIGS. 1 and 2 and, in particular, spacer 15 and sleeve 16 which hold the tines 12 and 14 in place. This arrangement is particularly advantageous in that the use of rivets which are conventionally employed to hold forceps tines in place are avoided. Further, the forceps are easily assembled or taken apart as will be apparent from the following description. The spacer comprises a wedge-shaped member having outwardly extending pins 104 through 108 disposed on one side thereof and outwardly extending pins 110 through 114 disposed on the other side thereof. The tines 12 and 14 are provided with openings through which the projections 104 through 114 extend. Sleeve 16 is provided with a pair of openings 116 and 118 through which pins 104 and 110 extend. In assembling the forceps, the sleeve 16 is simply pushed over the assembled tines and snapped onto pins 104 and 110. A wedge-shaped opening 120 may be provided in spacer 15 to facilitate the snapping on of sleeve 16 and the closing of the forceps.

The spacer 15 may also be provided with a rearwardly extending strain-relief portion 122, which is stepped, as shown at 124. Sleeve 16 has an opening 126 in the end thereof through which cord 18 extends. Further, the inner portion of sleeve 16 near opening 126 may also be stepped as shown at 128. Thus, the cord 18 preferably extends between the stepped portions 124 and 128 to provide strain relief therefor. As previously discussed, opening 70 may extend through spacer 15 to accommodate monopolar embodiments. The spacer 15 and sleeve 16 are preferably made from hard plastic. As shown in FIG. 2, the tines 12 and 14 preferably have thinner portions 130 and 132, the thickness of which can be so selected as to facilitate ease of closing the forceps.

In operation, the physician manually actuates switch 32 in the embodiments of FIGS. 1 and 8 by pressing flexible cap 38 in a direction substantially parallel to the longitudinal axis of the forceps. In any event, the actuation does not occur in a direction which is substantially perpendicular to the latter axis as is the case, for example, in the aforementioned Bagley patent. By so actuating the switch, spring 36 is radially brought into electrical contact with post 34 thereby closing the switch and energizing the forceps in a well known manner, as described, for example, in the Bagley patent. Thus, actuation of the switch is independent of the closing of the forceps thereby providing the physician with a greater degree of flexibility in performing a procedure.

Referring to the FIG. 9 embodiment, switch 32 is actuated by the closing of the forceps. In particular, springs 36 and 92 will be brought into engagement when the forceps are closed, as can be appreciated from FIGS. 8 and 9. This arrangement is particularly advantageous in that the electrical contacts comprising springs 36 and 92 are covered by flexible cap 38 which is made of an electrically insulative material, such as rubber, and thus, there is no danger of exposure to these contacts as is the case with the forceps disclosed in the Bagley patent.

It should be understood that the double spring embodiment of FIG. 9 can, of course, be employed in the outside switch arrangement of FIGS. 1 and 8, while the single spring post arrangement of FIGS. 1 and 8 could be employed in the inside switch arrangement of FIG. 9. However, if the latter arrangement were employed, the center post should preferably be made of a flexible, electrically conductive material to facilitate closing of the forceps.

As indicated hereinbefore, the tines 12 and 14 can comprise circuit boards made, for example, from a glass epoxy material with circuit paths 40–44 disposed thereon. Further in order to insulate any exposed conductive material, the circuit boards may be dip coated. However, in a dip coating process, there is little, if any, control of the outside shape of the product. Only if the shape of the circuit board or other substrate structure is very close to the desired outside shape can dip coating be used. This is the process normally used on electrosurgical forceps.

Insert molding has been proposed for electrosurgical instruments wherein wires can be embedded in a tine or the like during a molding process in which the part is formed. See, for example, U.S. Pat. No. 1,814,791 where this process is suggested for making certain electrosurgical instruments. Insert molding would apparently be ideal for the manufacture of forceps or other electrosurgical instruments in that the desired shape can be controlled with the wires safely buried deep inside the product. However, the use of insert molding with fine wires suspended inside is not practical for parts such as the tines of an electrosurgical forceps. Thus, when rather fragile parts such as fine electrical wires are to be embedded in plastic there is no way to hold these in place and guarantee their safety during the insert molding process. For example, it might be possible to tightly suspend a small wire across the mold cavity such that the extremely high pressures of inflowing plastic would not destroy it as the plastic distributed itself around it. However, if the wire were not straight — i.e. the plastic channel were curved as in a forceps, then there is no way to support such a wire adequately for the insert molding process. The use of heavy wires that would not be significantly deflected in the molding process is limited by the flexibility requirements of the forceps arms. Thus, it is impractical to use the insert molding process where the wires are initially molded in place for making electrosurgical forceps and similar instruments.

In various attempts to overcome the foregoing problems, different solutions were attempted in accordance with the invention. Thus, referring to FIG. 10, the entire forceps was molded as a molded fork assembly with the electrical conductors 40 and 42 disposed on the inside of a flexible printed circuit board 134 glued to a groove disposed on the inside of tine 12 whereby the conductors were buried inside board 134. Although the resulting forceps is rather sophisticated, it is somewhat difficult to make, in that skill and care are required in its assembly. Further, the process is not easily adapted to automation nor are parts costs low enough. In fact, the foregoing shortcomings also apply to the previously discussed processes.

The procedure next attempted was to mold the basic fork assembly with recesses for the wires in the inside surfaces. This required insulated wires and involved somewhat difficult assembly practices. Next, the fork was turned inside-out such that the recesses were on the outside of the fork. This facilitated the wiring assembly. Covers could then be glued on to cover the wires. Alternatively, the cost and mess of gluing can be avoided by placing the wired fork into an injection mold, and molding a cover 136 in place, as shown in FIG. 11. It should be noted that cover 136 is on the outside of the fork. Further, the conductors 40 and 32 may be No. 24 copper wires, for example. Interlocks may be provided so that cover 136 is effectively staked in place, see FIGS. 12–14. The fit is totally intimate. The forceps tips 20 and 22 may be locked into the plastic via notches and/or offsets or, preferably, they may be insert molded into the fork structure at the time the fork is molded. Due to the heavier construction of the tips, they readily lend themselves to the insert molding process.

Referring to FIG. 15, there is an illustrative molded fork after the first molding step, after which wires 40 through 44 are inserted therein. Grooves 138 and 139 are provided along the insides of tines 12 and 14. On the proximal side of switch 32, groove 138 (see FIG. 17) is provided with two recesses in which conductors 40 and 42 are inserted, while on the distal side thereof (see FIG. 16) the groove is provided with a single recess for conductor 40. As previously stated, tips 20 and 22 may be insert molded into tines 12 and 14 respectively during the molding of the fork assembly. The conductors 40 and 44 may be spot welded to tips 20 and 22 at 140 and 144 where openings 146 and 148 may be provided in the molded fork to facilitate the spot welding.

Wire 40 is also spot welded to post 34 while wire 42 is welding to spring 36. The molded fork assembly also has incorporated therein grooves 150 and 152 and openings 154 and 156 whereby groove 150 communicates with groove 138 via opening 154 and groove 152 communicates with groove 139 via opening 156. Thus, wires 40 and 44 extend from tips 20 and 22 to the proximal end of the fork indicated at 158 and 160 while wire 42 extends from spring 36 to proximal end 158.

Once the tips 20 and 22 and the spring 36 and post 34 have been electrically connected to the inserted wires 40 through 44 as discussed above, the entire assembly is then placed in a second mold to fill the grooves for the wires 40 through 44 and the openings 140, 148, 154 and 156.

The fork member is also provided with pins 104 and 110 to permit the snapping of sleeve 16 over the distal end. Thus, the wires of cord 18 can then be connected to the wires 40 through 44 depending on the desired mode of operation. After the wires have been connected, the sleeve 16 can be slipped over the proximal end of the fork and snapped onto pins 104 and 110.

The double molding process of this invention thus provides a method for making an electrosurgical forceps or the like by first molding a plastic-only part which has retaining grooves to hold fine wires in desired configurations. With the wire safely inserted in the groove and electrically connected to the tips and switching assembly, if used, the part is then placed into a second mold which injects plastic to cover the groove and seal the small wire safely into the center of the plastic part.

What is claimed is:

1. An electrosurgical forceps comprising:
a first tine having a distal end and a proximal end;
a second tine having a distal end and a proximal end, said first and second tines being flexibly mounted with respect to each other with said distal ends being adjacent one another;
switching means mounted on only one of said tines, said switching means being manually operable to effect the closure thereof and comprising a first conductive member mounted with respect to and extending substantially perpendicularly from said one tine and a second conductive member comprising a flexible member concentrically disposed about and spaced from said first member and mounted with respect to said one tine so that said switching means may be manually closed by applying pressure to said flexible member until it engages said first member;
first and second electrically conductive contacts mounted on said one tine respectively contacting said first member and said flexible member of the switching means, said contacts being adapted for connection to an electrosurgical energy source; and
means disposed on said distal ends of said tines for applying said electrosurgical energy to a patient through said contacts upon closure of said switching means.

2. A forceps as in claim 1 wherein said forceps further include a flexible, electrically insulative covering enclosing said contacts to prevent exposure thereof.

3. A forceps as in claim 1 where said means for applying electrosurgical energy to said patient includes (a) a first terminal disposed at the proximal end of said one tine, (b) a second terminal disposed at the proximal end of said tine, (b) a second terminal disposed at the proximal end of said one tine, (c) a third terminal disposed at the proximal end of the other tine, (d) a first electrically conductive path disposed on and extending from said distal end of said one tine to said first terminal at the proximal end thereof, one of said first and second conductive members being electrically connected at its conductive contact to said first electrically conductive path, (e) a second electrically conductive path disposed with respect to said one tine extending from said second terminal disposed at said proximal end thereof to the conductive contact of the other conductive member of said switching means, and (f) a third electrically conductive path disposed with respect to the other tine and extending from said distal end thereof to said third terminal located at the proximal end thereof
the foregoing arrangement of circuit paths enabling said forceps to be used either in a monopolar mode with or without switching or a bipolar mode with or without switching.

4. A forceps as in claim 1 where said first tine has at least one opening disposed at the proximal end thereof; said second tine has at least one opening disposed at the proximal end thereof; and said forceps includes a spacer member for separating said first and second tines disposed therebetween at said proximal ends thereof, said spacer member having outwardly projecting pins respectively extending through said openings in said tines; and
a removable sleeve having distal and proximal ends and first and second openings extending through the distal end thereof, said sleeve being removably disposed about the proximal ends of said tines and said pins respectively extending through said first and second openings of the sleeve to removably hold said tines in place 5. A forceps as in claim 4 where said spacer member has a proximal end and includes a strain-relief member extending from the proximal end thereof and said sleeve having an opening in the proximal end thereof, said first and second tines each having connecting means for establishing an electrical connection to said means for applying electrosurgical energy and said forceps including an electrical cord, said cord extending through the opening in the proximal end of said sleeve and electrically connected to the connecting means of said first and second tines, said strain-relief member engaging said cord to provide strain relief therefor.

6. A forceps as in claim 1 where said one tine has an outside surface and said switching means is mounted on the outside surface of said one tine.

7. A forceps as in claim 6 where said first member is a post and said flexible member is a coil spring concentrically disposed about said post.

8. A forceps as in claim 1 where said one tine has an inside surface and said switching means is mounted on the inside surface of said one tine.

9. A forceps as in claim 8 where said first member is a first coil spring and said flexible member is a second coil spring concentrically disposed about said first coil spring.

10. A forceps as in claim 1 where said first member is flexible.

11. A forceps as in claim 10 where said first member is a coil spring.

12. A forceps as in claim 1 where said flexible member is a coil spring.

13. A forceps as in claim 12 where said first member is also a coil spring.

* * * * *